(12) United States Patent
Gupta et al.

(10) Patent No.: US 11,020,214 B2
(45) Date of Patent: Jun. 1, 2021

(54) DEVICES, SYSTEMS, AND METHODS FOR PYLORIC OCCLUSION

(71) Applicant: Boston Scientific Scimed, Inc., Maple Grove, MN (US)

(72) Inventors: Saurav V. Gupta, Medway, MA (US); Camron Hagemeyer, Bloomington, IN (US); Marc A. Barthet, Marseilles (FR); Jean-Michel Gonzalez, Marseilles (FR); Darren Curran, Galway (IE); Dan Bacon, Fitchburg, MA (US); Peter L. Dayton, Brookline, MA (US); Douglas Melanson, Natick, MA (US); Gerard Duignan, Roscommon (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 103 days.

(21) Appl. No.: 16/361,772

(22) Filed: Mar. 22, 2019

(65) Prior Publication Data
US 2019/0298559 A1     Oct. 3, 2019

Related U.S. Application Data

(60) Provisional application No. 62/650,080, filed on Mar. 29, 2018, provisional application No. 62/650,075, filed on Mar. 29, 2018.

(51) Int. Cl.
*A61F 2/04*     (2013.01)
*A61B 1/018*    (2006.01)
(Continued)

(52) U.S. Cl.
CPC ............. *A61F 2/04* (2013.01); *A61B 1/018* (2013.01); *A61B 1/2733* (2013.01);
(Continued)

(58) Field of Classification Search
CPC ............. A61F 2/04; A61F 2002/045; A61F 2220/0008; A61F 2230/0095;
(Continued)

(56) References Cited

U.S. PATENT DOCUMENTS

| 3,913,568 A | 10/1975 | Carpenter |
| 5,842,973 A | 12/1998 | Bullard |

(Continued)

FOREIGN PATENT DOCUMENTS

| EP | 1420730 A2 | 5/2004 |
| WO | WO2003017882 A2 | 3/2003 |

OTHER PUBLICATIONS

International Search Report and Written Opinion for International application No. PCT/US2019/023604, dated Jun. 25, 2019, 14 pages.

*Primary Examiner* — Richard G Louis

(57) ABSTRACT

According to exemplary embodiments of the present disclosure, devices, systems, and methods for pyloric occlusion in an endoscopic procedure may include a first flange and a second flange connected to the first flange by a saddle region having a lumen. The second flange may be proximal to the first flange. The pyloric occlusion device may further include a closure element. The closure element may be configured to occlude a flow of material through the lumen, including across the pylorus when deployed. The closure element may be a closure of the lumen by rotation of one of the first or second flanges about the saddle region relative to the other of the first or second flange.

20 Claims, 15 Drawing Sheets

(51) Int. Cl.

| | | |
|---|---|---|
| *A61B 1/273* | (2006.01) | |
| *A61B 17/11* | (2006.01) | |
| *A61B 17/29* | (2006.01) | |
| *A61F 5/00* | (2006.01) | |
| *A61B 5/06* | (2006.01) | |
| *A61B 90/30* | (2016.01) | |
| *A61B 90/00* | (2016.01) | |
| *A61B 17/00* | (2006.01) | |
| *A61M 25/01* | (2006.01) | |
| *A61B 17/12* | (2006.01) | |
| *A61B 17/30* | (2006.01) | |

(52) U.S. Cl.
CPC ............ *A61B 1/2736* (2013.01); *A61B 5/061* (2013.01); *A61B 17/1114* (2013.01); *A61B 17/29* (2013.01); *A61B 90/30* (2016.02); *A61F 5/0079* (2013.01); *A61F 5/0089* (2013.01); *A61B 17/12031* (2013.01); *A61B 17/12099* (2013.01); *A61B 17/12172* (2013.01); *A61B 2017/00221* (2013.01); *A61B 2017/00278* (2013.01); *A61B 2017/00336* (2013.01); *A61B 2017/00818* (2013.01); *A61B 2017/00862* (2013.01); *A61B 2017/00867* (2013.01); *A61B 2017/1125* (2013.01); *A61B 2017/1139* (2013.01); *A61B 2017/2924* (2013.01); *A61B 2017/2944* (2013.01); *A61B 2017/305* (2013.01); *A61B 2090/0811* (2016.02); *A61B 2090/306* (2016.02); *A61B 2090/309* (2016.02); *A61B 2090/3945* (2016.02); *A61F 2002/045* (2013.01); *A61F 2220/0008* (2013.01); *A61F 2230/0095* (2013.01); *A61F 2250/0059* (2013.01); *A61M 2025/0166* (2013.01)

(58) Field of Classification Search
CPC ............ A61F 2250/0059; A61F 5/0079; A61F 5/0089; A61B 17/1114; A61B 17/12099; A61B 2017/1125; A61B 17/12172; A61B 2090/3945; A61B 2017/00221; A61B 2017/00336; A61B 2017/00818; A61B 2017/00862; A61B 2017/1139; A61B 5/061; A61B 90/30; A61B 1/2736; A61B 1/018; A61B 1/2733; A61B 17/29; A61B 2090/0811; A61B 2017/00867; A61B 17/12031; A61B 2017/305; A61B 2090/306; A61B 2090/309; A61B 2017/00278

See application file for complete search history.

(56) References Cited

U.S. PATENT DOCUMENTS

| | | |
|---|---|---|
| 7,559,925 B2 | 7/2009 | Goldfarb et al. |
| 8,211,186 B2 | 7/2012 | Belhe et al. |
| 8,361,041 B2 | 1/2013 | Fang et al. |
| 9,044,300 B2 | 6/2015 | Belhe et al. |
| 9,089,258 B2 | 7/2015 | Goldfarb et al. |
| 9,282,986 B2 | 3/2016 | Hanson et al. |
| 9,433,343 B2 | 9/2016 | Drontle et al. |
| 9,486,614 B2 | 11/2016 | Drontle et al. |
| 9,622,897 B1 | 4/2017 | Stangenes et al. |
| 9,730,822 B2 | 8/2017 | O'Neill et al. |
| 10,130,502 B2 | 11/2018 | Chamorro et al. |
| 10,307,280 B2 | 6/2019 | Zeiner et al. |
| 10,420,665 B2 | 9/2019 | Sharma et al. |
| 2005/0273060 A1* | 12/2005 | Levy .................... A61F 5/0083 604/192 |
| 2006/0271024 A1 | 11/2006 | Gertner et al. |
| 2009/0082644 A1* | 3/2009 | Li ....................... A61B 5/14539 600/302 |
| 2009/0093837 A1* | 4/2009 | Dillon .................. A61F 5/0079 606/191 |
| 2010/0016885 A1 | 1/2010 | Eidenschink et al. |
| 2012/0172665 A1 | 7/2012 | Allyn et al. |
| 2012/0184980 A1* | 7/2012 | Anderson ............ A61F 2/0036 606/192 |
| 2013/0030351 A1* | 1/2013 | Belhe ................... A61F 5/0076 604/9 |
| 2014/0088359 A1 | 3/2014 | Quaye |
| 2014/0155928 A1 | 6/2014 | Fabian et al. |
| 2014/0236064 A1 | 8/2014 | Binmoeller et al. |
| 2015/0374383 A1* | 12/2015 | Bodewadt ........ A61B 17/12172 606/157 |
| 2017/0000990 A1 | 1/2017 | Gerrans et al. |
| 2017/0296037 A1 | 10/2017 | Yoshino |
| 2017/0333240 A1 | 11/2017 | Stangenes et al. |
| 2017/0367711 A1 | 12/2017 | Bödewadt et al. |
| 2018/0000499 A1 | 1/2018 | Altman et al. |

\* cited by examiner

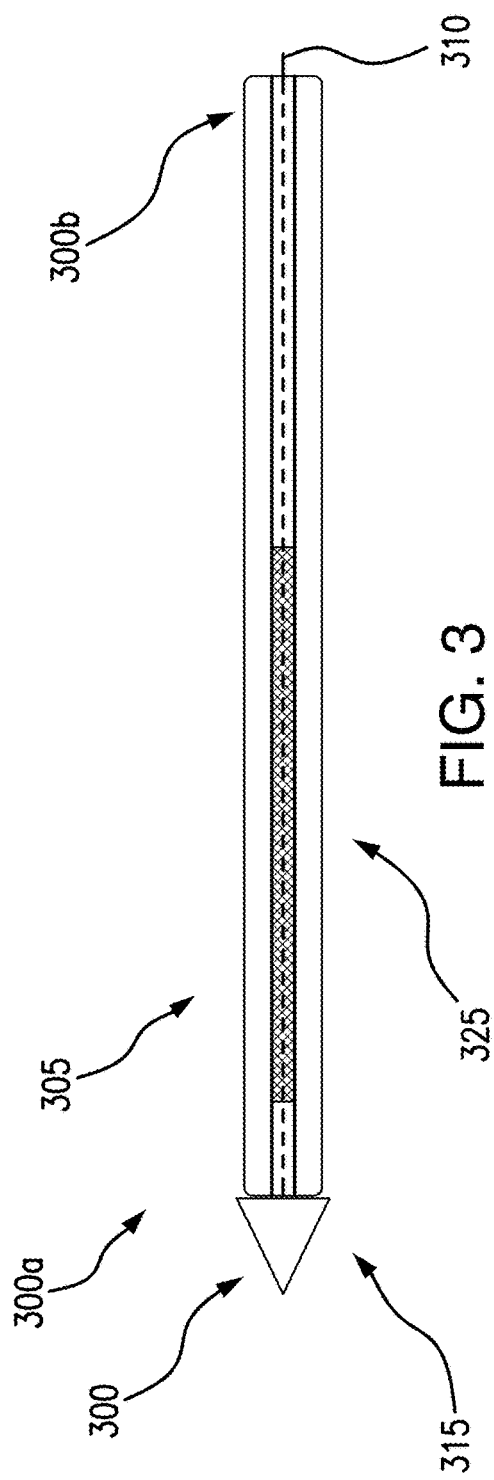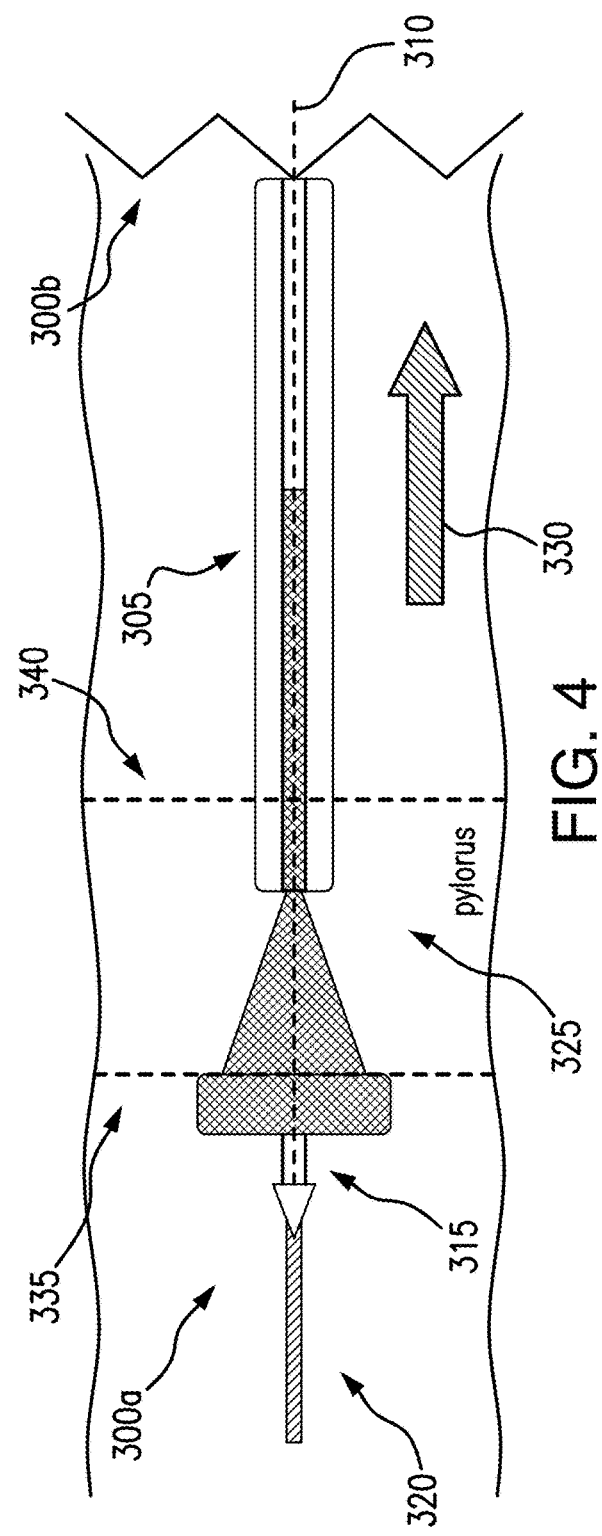

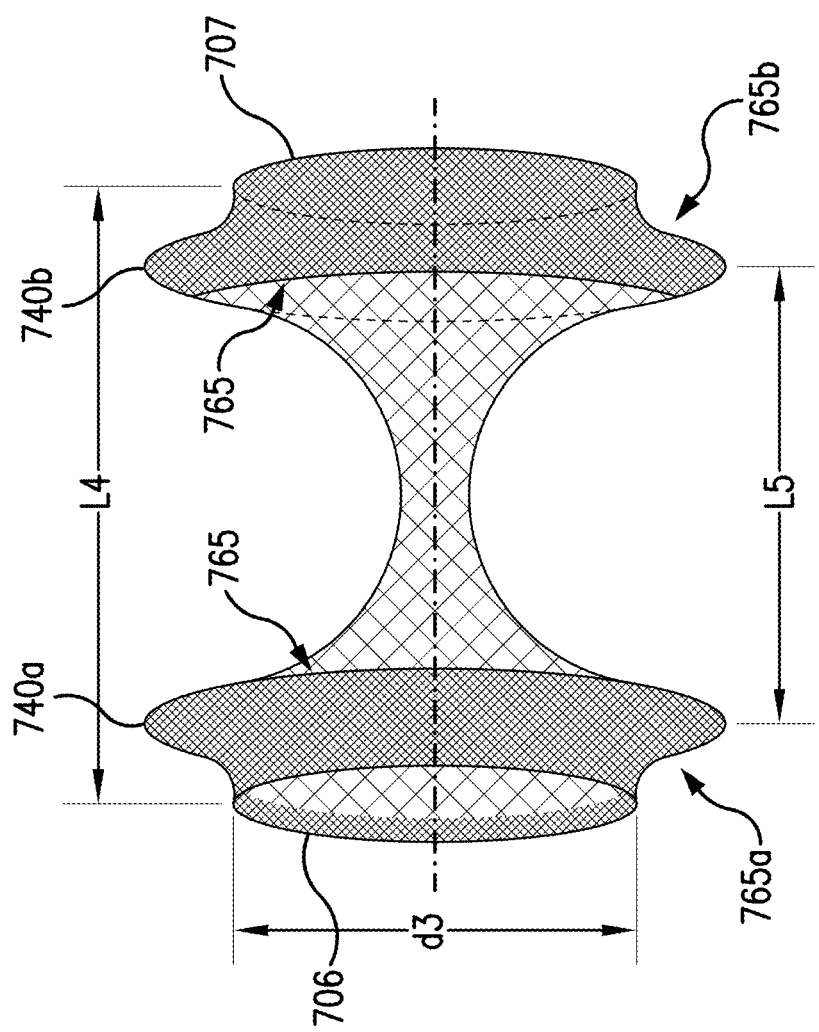

DEVICES, SYSTEMS, AND METHODS FOR PYLORIC OCCLUSION

CROSS-REFERENCE TO RELATED APPLICATIONS

This application is a non-provisional application of, and claims the benefit of priority to, U.S. Provisional Application Ser. No. 62/650,080, filed Mar. 29, 2018, entitled "Devices, Systems, and Methods for Pyloric Occlusion," and to U.S. Provisional Application Ser. No. 62/650,075, filed Mar. 29, 2018, entitled "Systems and Methods for Performing Endoscopic Procedures," the entirety of which both applications are expressly incorporated by reference herein.

FIELD

The present disclosure relates generally to systems and methods for performing endoscopic procedures, and, more particularly, to devices, systems, and methods for occluding the pylorus during gastrojejunostomy procedures.

BACKGROUND

Obesity affects a growing population and may cause additional diseases such as type 2 diabetes, greatly increasing risk of a patient's health. Surgical procedures such as bariatric surgery, e.g., to restrict a portion of a stomach and/or bypass portions of the intestine, may be the only option for patients categorized as morbidly obese. Additionally, these types of procedures may have significant side effects, such as enteric hormonal changes, and are relatively invasive surgical procedures with associated complications, tissue trauma, and/or infections, which in some instances may put the patient at risk.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a pyloric occlusion device for deployment in an endoscopic procedure may include a first flange and a second flange connected to the first flange by a saddle region having a lumen. The second flange may be proximal to the first flange. The pyloric occlusion device may further include a closure element, wherein the closure element may be configured to occlude a flow of material through the lumen.

In various of the foregoing and other embodiments of the present disclosure, the closure element may be a closure of the lumen by rotation of one of the first or second flange relative to the other of the first or second flange, or by rotation of the first and second flange opposite of each other. The closure element may be a swaged pin disposed proximal to the second flange. The closure element may be a fastener. The closure element may be a plug to fill the lumen. The closure element may be a filter, and the filter may include one or more hooks extending from the saddle region. The first flange may include a bulb and the second flange may include a duodenal extension. The pyloric occlusion device may be formed of a braided self-expanding material. The braided material may be concentrated at the closure element. A first diameter of the first flange may be equal to a second diameter of a second flange. A first diameter of the first flange may be different from a second diameter of a second flange. The pyloric occlusion device may further include one or more mechanical fasteners disposed around the second flange for anchoring the second flange to tissue. A covering may be disposed on a least a portion of the first flange, second flange, or lumen, or combinations thereof, for preventing tissue ingrowth. The covering may include a membrane, sleeve, or coating, or combinations thereof. The pyloric occlusion may be deployable across a pylorus with the saddle region bridging the pylorus, the first flange may be anchored against a duodenum side of the pylorus, the second flange may be anchored against a gastric side of the pylorus, and the closure element may be operable to occlude the flow of material through the pylorus. The pyloric occlusion device may be removable to allow flow of material through the pylorus.

According to an exemplary embodiment of the present disclosure, a system for delivering an occlusion device to a pylorus in an endoscopic procedure may include a delivery device including an inner member having a guidewire and a retractable outer sheath. The inner member and the outer sheath may be operable to constrain the occlusion device therebetween prior to deployment. The occlusion device may include a first flange, and a second flange may be connected to the first flange by a saddle region having a lumen. The second flange may be proximal to the first flange. The system may further include a closure element, wherein the closure element is configured to occlude a flow of material through the lumen.

In various of the foregoing and other embodiments of the present disclosure, the closure element may be a closure of the lumen by rotation of one of the first or second flange relative to the other of the first or second flange, or by rotation of the first and second flange opposite of each other. The closure element may be any of the following: a swaged pin disposed proximal to the second flange; a fastener; a plug to fill the lumen; or a filter, where the filter may include one or more hooks extending from the saddle region. The pyloric occlusion may be deployable across a pylorus with the saddle region bridging the pylorus. One of the first flange or the second flange may be anchored against a duodenum side of the pylorus, and the other of the first flange or the second flange may be anchored against a gastric side of the pylorus, and the closure element may be operable to occlude the flow of material through the pylorus.

According to an exemplary embodiment of the present disclosure, a method for delivering an occlusion device to a pylorus in an endoscopic procedure may include inserting an endoscope in a stomach of patient and deploying a delivery device through the endoscope to a position proximal to the pylorus for delivering the occlusion device across the pylorus. The delivery device may include a sheath for holding the occlusion device in a constrained configuration. The method may further include extending the delivery device at least partially through the gastric tissue through the pylorus, and retracting the sheath to deploy a first flange on the duodenal side of the pylorus, and retracting the sheath further to deploy a second flange on the gastric side of the pylorus. The first flange and the second flange may be connected by a saddle region having a lumen. The occlusion device may include a closure element operable to occlude a flow of material through the pylorus.

In various of the foregoing and other embodiments of the present disclosure, the method may further include removing the occlusion device from the pylorus. The closure element may be any of the following: a closure of the lumen by rotation of one of the first or second flanges relative to the other of the first or second flange; a swaged pin disposed proximal to the second flange; a fastener; a plug disposed in the lumen; or a filter, where the filter may include one or more hooks extending from saddle region. The pyloric occlusion device may be formed of a braided self-expanding material. The first flange may include a bulb and the second flange may include a duodenal extension. The method may further include one or more mechanical fasteners disposed around the second flange for anchoring the second flange in tissue.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 3 illustrates an exemplary embodiment of a delivery device for a pyloric occlusion device in accordance with the present disclosure;

FIG. 4 illustrates an exemplary embodiment of a delivery device for a pyloric occlusion device in a partially deployed state in accordance with the present disclosure;

FIGS. 7, 7A, and 8 illustrate an exemplary embodiment of a pyloric occlusion device in accordance with the present disclosure;

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

It may be understood that references to "proximal" may be defined as an end of the systems and devices closest to the entry point of the patient (e.g., a nasal and/or oral cavity) and "distal" may be defined as an end of the systems and devices closest to the desired location of the system and devices in the patient (e.g., a patient's gastrointestinal system such as the jejunum).

Figure 1:
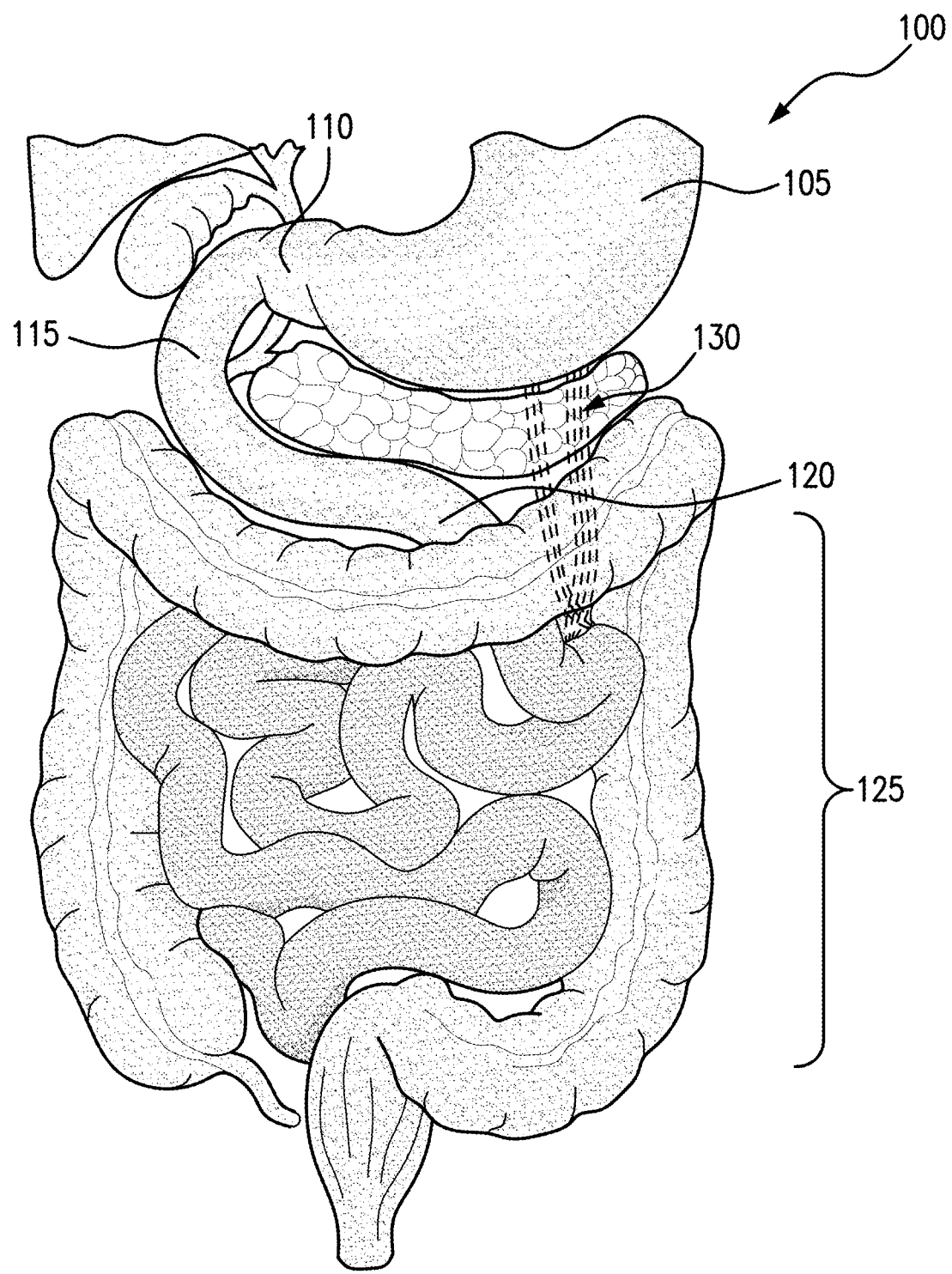
FIG. 1 illustrates a human gastrointestinal system.

FIG. 1 illustrates a gastrointestinal system 100 of a patient. According to exemplary embodiments of the present disclosure, a natural orifice transluminal endoscopic surgery (NOTES) procedure may be advantageous over other types of bypass procedures from a stomach 105 to a jejunum 120 (e.g., an endoscopic ultrasound procedure) so that a jejunal loop, or a loop of small bowel in the jejunum, may be selected a distance from the pylorus 110. In some embodiments, an anastomosis may be created into the jejunum 120 in a region that may not otherwise be reachable using other systems. In this manner, stomach content (e.g., food and other nutrients) may not be absorbed as it travels from the stomach 105 through the small bowel 125, promoting patient weight loss and possibly controlling type-2 diabetes. For example, the hindgut hypothesis states that diabetes control results from the more rapid delivery of nutrients to the distal small intestine, thereby enhancing the release of hormones such as glucagon-like peptide-1 (GLP-1). The Foregut hypothesis states that exclusion of the proximal small intestine reduces or suppresses the secretion of anti-incretin hormones, leading to improvement of blood glucose control. Thus, type-2 diabetes may be controllable, along with weight loss, by bypassing a longer portion of the jejunum 120, e.g., creating an anastomosis approximately 150 cm or greater from the pylorus 110 at the duodenum 115.

The present disclosure relates to devices, systems, and methods for occluding a pylorus during an endoscopic, laparoscopic, and/or open surgical procedure, e.g., for creating a gastrojejunal anastomosis, as described in pending application filed concurrently, entitled "Systems and Methods for Endoscopic Procedures,", which is herein incorporated by reference in its entirety. For example, occluding duodenal access and redirecting food, liquid, and other nutrients through an alternative path, effectively bypassing the pancreas or at least delaying interaction of the stomach content with digestive enzymes until further down the small bowel, may reduce obesity and a subsequently a patient's risk of type-2 diabetes. In some embodiments, a pyloric closure device may be reversible, e.g., a medical professional may be able to delivery and/or remove the device endoscopically. Although the devices, systems, and methods are described herein with respect to a gastrointestinal system, it may be understood that exemplary embodiments of devices, systems, and methods in accordance with the present disclosure may be advantageous for use in any other procedures and/or anatomy, for deployment of an occlusion device to prevent movement of material.

Figure 2B:
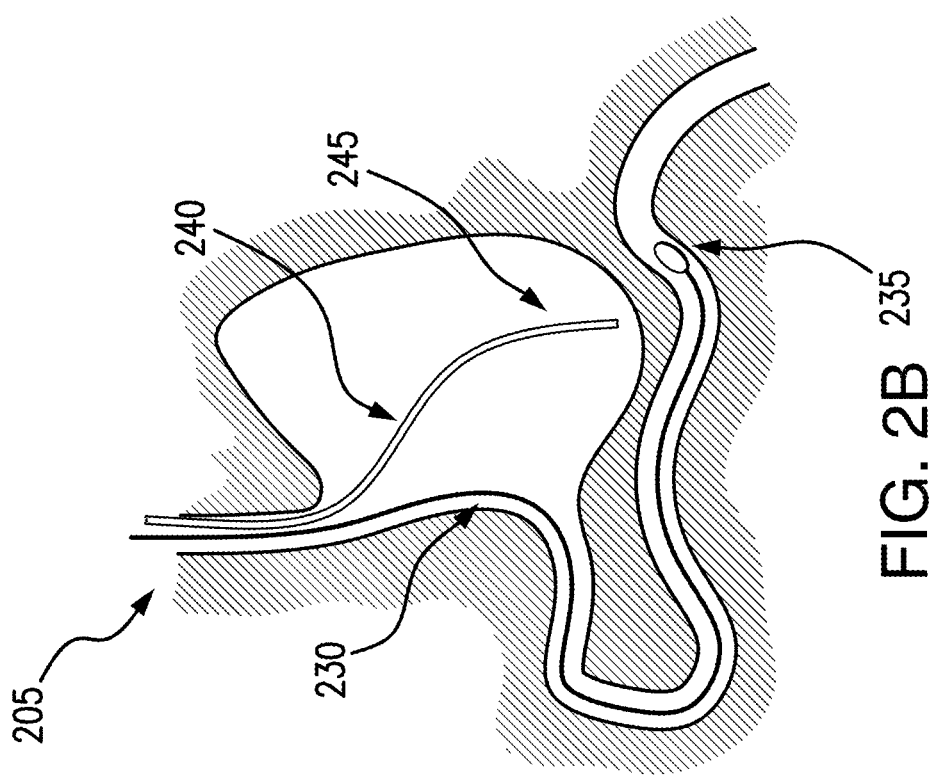
FIGS. 2A-2F illustrate an exemplary embodiment of a process for creating an anastomosis in accordance with the present disclosure.
Figure 2A:
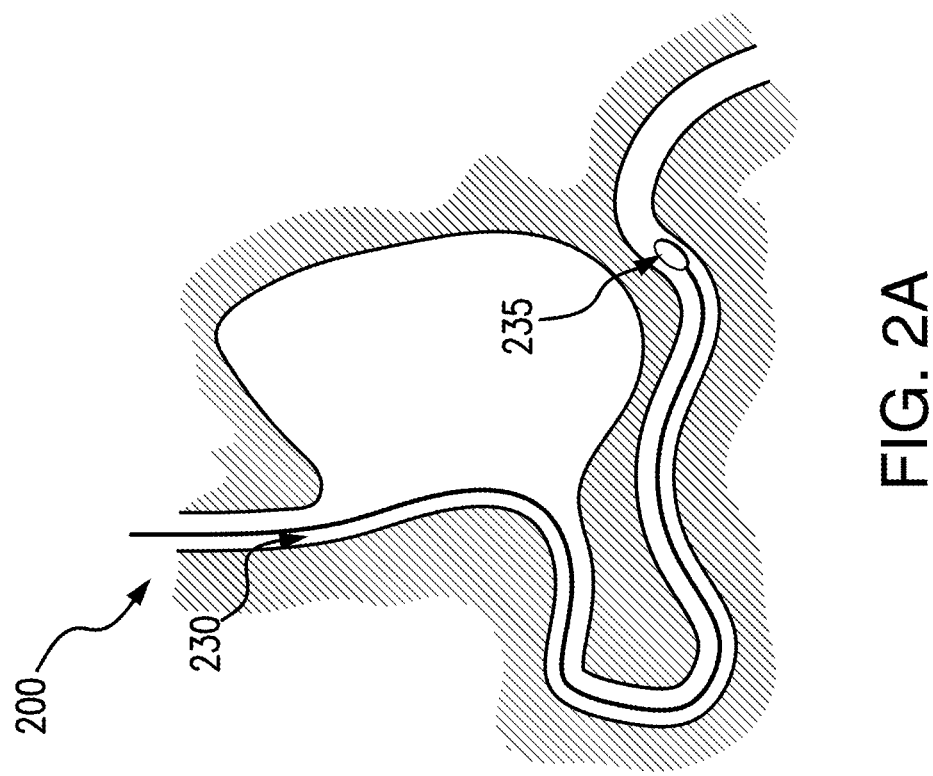

Referring now to FIGS. 2A-2F, schematics of an exemplary embodiment of an endoscopic procedure, e.g., a gastrojejunostomy, in accordance with the present disclosure, are shown. For example, as shown in FIG. 2A, in a first step 200 a nasocatheter 230 may be inserted into a patient, e.g., through the nose and esophagus into a stomach and into a small bowel or jejunum. A distal end 235 of the nasocatheter may be positioned a desired distance in the jejunum as determined by the medical professional. The nasocatheter may be allowed to migrate some portion of the way into position, e.g., by peristaltic motion acting upon projections on the exterior of the catheter. At step 205, an endoscope 240 may be inserted into a patient's stomach, so that a distal end 245 is positioned in the stomach at a region near the distal end 235 of the nasocatheter 230 in the small bowel.

Figure 2C:
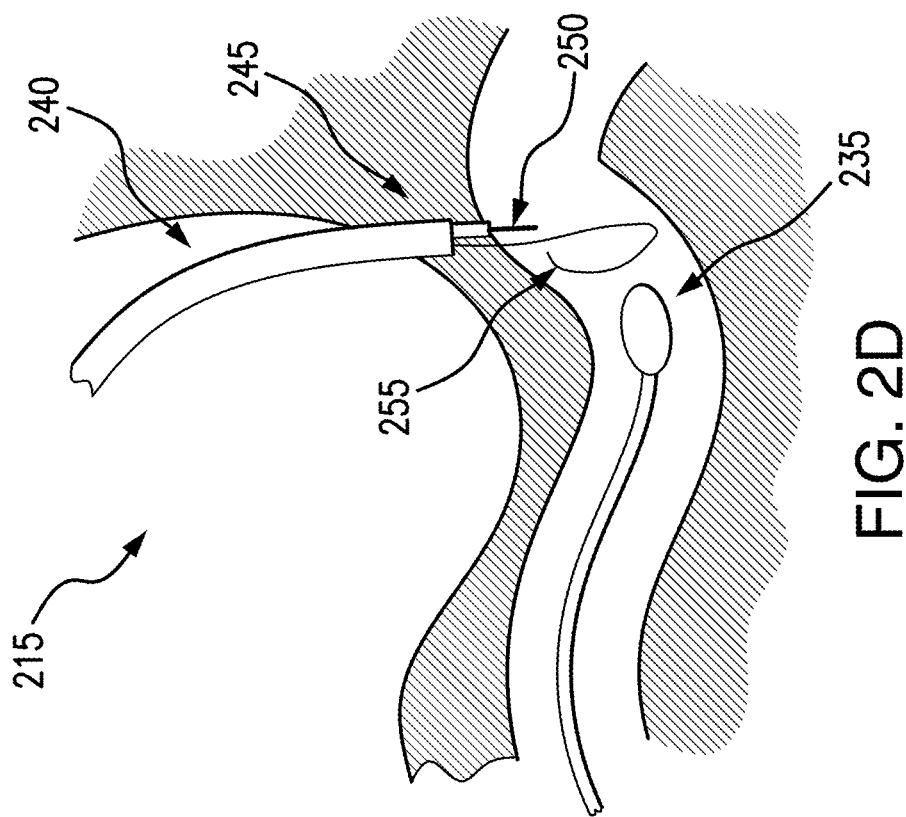

When the distal end 245 of the endoscope 240 is in the desired position, FIG. 2C shows step 210, where the stomach wall may be perforated so that an accessory may be extended to tissue of the small bowel in the region of the distal end 235 of the nasocatheter 230. For example, a grasping system having an end effector 250 at a distal end may be extended out of the endoscope 240. The end effector 250 may grasp and hold tissue of the small bowel at a position indicated by the nasocatheter 230, so that an anastomosis may be formed in a desired position. For example, a light source emission that may be colored or a magnetic field at a distal end of the nasocatheter 230 may mark a position and guide a medical professional to make an incision at the marked position in the small bowel.

Figure 2D:
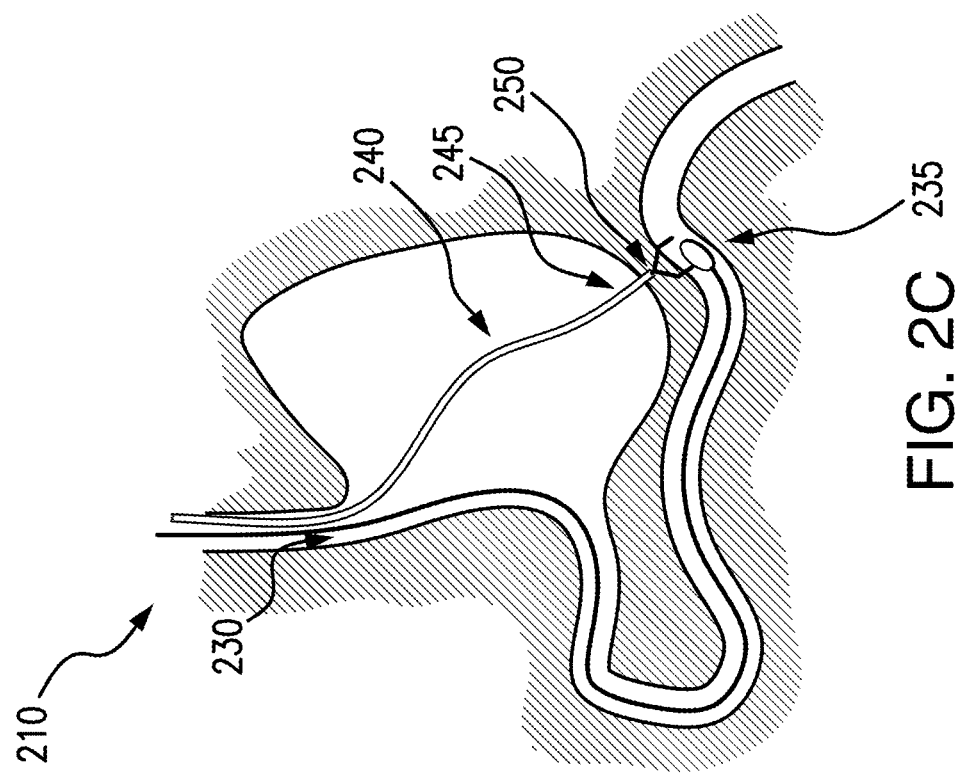

Referring now to FIG. 2D, at step 215, a needle 255 or other perforation mechanism may pierce the small bowel, and a guidewire may hold the position. The small bowel tissue may continue to be held by end effector 250 so the medical professional may be able to place an anastomosis device (e.g., implant) in the desired position. FIG. 2E shows that at step 220, an anastomosis stent 260 may be deployed from the nasocatheter 230. The stent 260 may join the patient's stomach to the small bowel, creating a bypass. For example, a delivery device may be inserted through the endoscope, possibly over the guidewire, through the opening in the stomach wall and opening in the jejunum, a distal retention member on the stent may be deployed inside the jejunum, the stent and delivery may then be retracted proximally to appose the small bowel against the stomach wall, at which point a proximal retention member on the stent may be deployed within the stomach to anchor the stent across the openings and create a bypass conduit for stomach content to flow through.

Figure 2F:
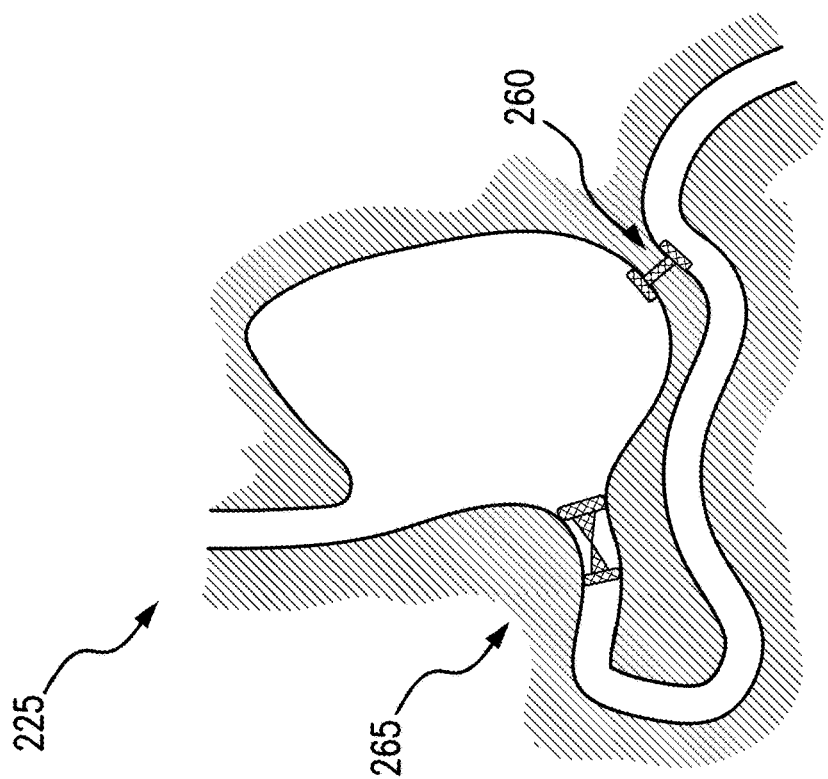
Figure 2E:
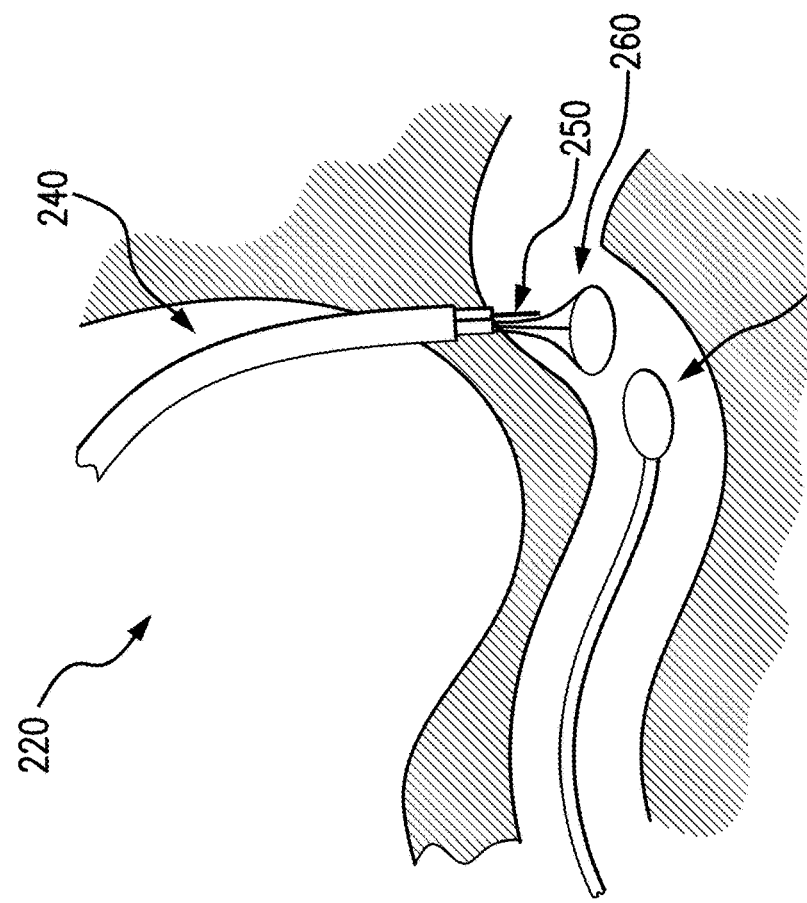

At step 225 illustrated at FIG. 2F, a pyloric occlusion device 265 may be deployed by the endoscope 240. For example, one or more accessories may be utilized to deliver an occlusion device to redirect a patient's stomach contents. The pyloric occlusion device 265 may be any configuration to prevent food, liquid, and/or other nutrients from flowing from the stomach into the duodenum (see FIGS. 5-9G). For example, food, liquid, and/or nutrients may flow from the stomach into the small bowel via the anastomosis stent 260, bypassing the duodenum. As described above, this may prevent or delay absorption in the patient's digestive tract, promoting weight loss and reducing risk of type-2 diabetes. To deploy the pyloric occlusion device, e.g., by a delivery device (see FIGS. 3-4), the medical professional may first remove the nasocatheter 230. In some embodiments, a medical professional may later retrieve the pyloric occlusion device 265, e.g., so that stomach contents may again flow from the stomach through the duodenum. For example, a delivery device may deliver and/or retrieve a pyloric occlusion device 265 endoscopically.

Figure 5:
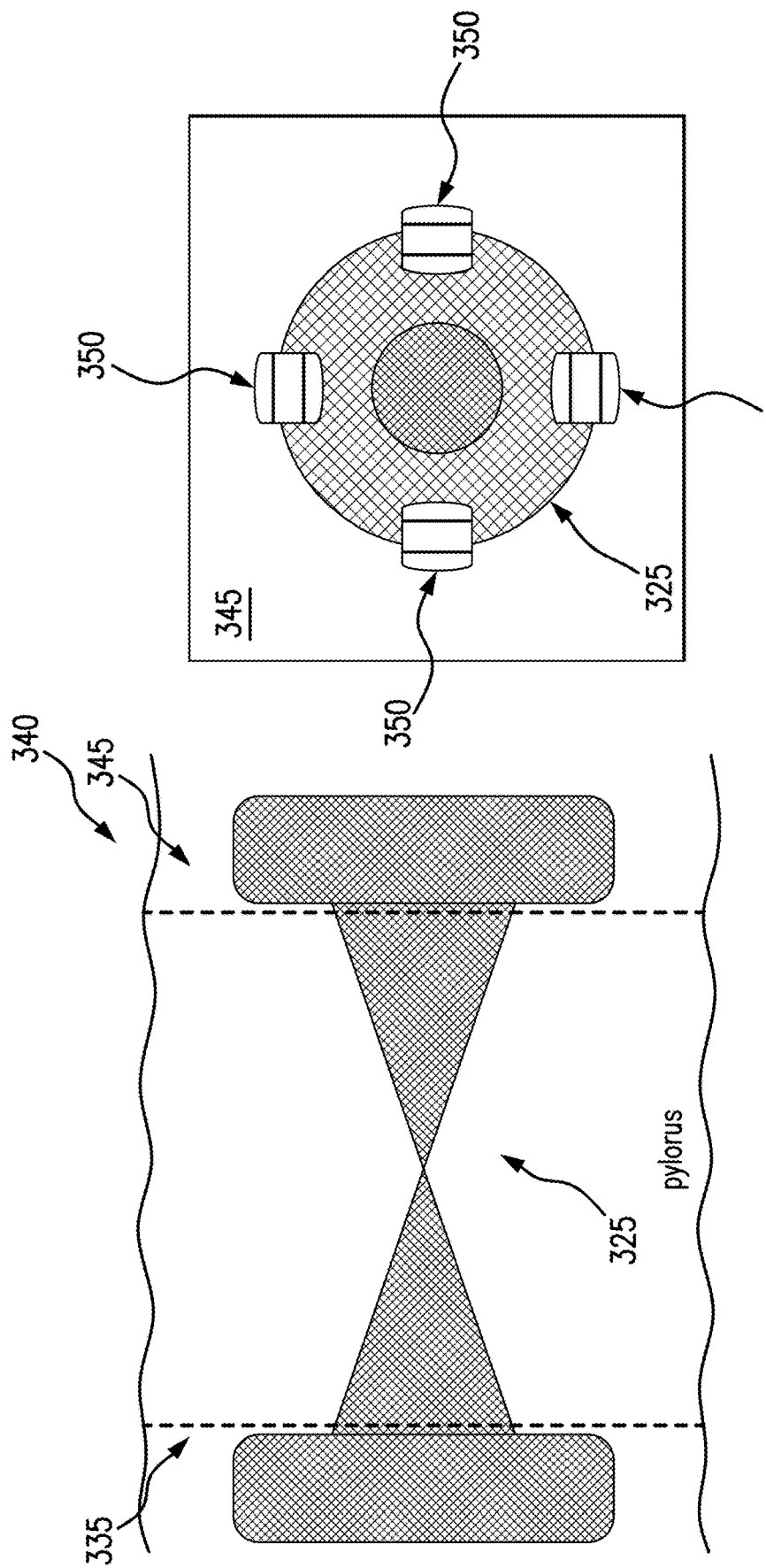
FIG. 5 illustrates an exemplary embodiment of a deployed pyloric occlusion device in accordance with the present disclosure.

FIGS. 3-5 illustrate an exemplary embodiment of delivery systems and devices in accordance with the present disclosure, for delivery through a scope (e.g., an endoscope such as endoscope 240. A delivery device 300 may include an outer sheath 305, e.g., a hollow tube extending along a longitudinal axis 310, for retaining the pyloric occlusion device in a compressed configuration. The delivery device 300 may be positionable at the desired location for delivering a pyloric occlusion device, e.g., between a duodenum tissue and a gastric tissue. An inner member 315 may extend through the outer sheath 305, and in some embodiments, the inner member 315 may be hollow, so that a guidewire 320 is extendable through the inner member 315 along the longitudinal axis 310 for extending into the duodenum wall 335. The inner member 315 and the outer sheath 305 may be configured to constrain a pyloric occlusion device 325. In embodiments, the pyloric occlusion device 325 may extend along the inner member 315, and the outer sheath 305 may retain the inner member 315 and the pyloric occlusion device 325 until the delivery device 300 is positioned for delivery. For example, the inner member 315 may include a recess for the pyloric occlusion device, and/or may include projections for retaining the pyloric occlusion device 325 to prevent slippage when the outer sheath 305 is being retracted. For example, when the inner member 315 extends from the stomach, e.g., gastric wall 340, through the pylorus and into the duodenum wall 335, the guidewire 320 may be inserted into the duodenum to guide the delivery device 300 for deployment of the pyloric occlusion device 325. In some embodiments, the outer sheath 305 may be controllable to partially deploy and/or reconstrain the pyloric occlusion device 325, to allow the medical professional to reposition the pyloric occlusion device 325 as desired before fully deploying. In some embodiments, the pyloric occlusion device 325 may include radiopaque markers, so that the medical professional may be able to monitor deployment with fluoroscopy, x-ray, and the like.

A pyloric occlusion device 325 may be formed as a closed stent, e.g., as shown in FIGS. 7, 7A, 8, 9A-9G and/or 10A-10B. As shown in FIG. 3, the pyloric occlusion device 325 may be compressed in the sheath 305 along the longitudinal axis 310. Once the guidewire 320 is positioned as desired by the medical professional, e.g., deployed from the stomach through the pylorus and into the duodenum (e.g., duodenum wall 335), the delivery device 300 may be extended along the guidewire 320 in a distal direction until the distal end 300a is positioned beyond the pylorus. The sheath 305 may then be retracted in a proximal direction along the guidewire 320 as indicated by arrow 330. In some embodiments, a push member may extend in a distal direction along the longitudinal axis 310 to act as backstop against the stent, when the sheath is retracted to deploy the pyloric occlusion device 325 from the sheath 305. As the sheath 305 is retracted, the pyloric occlusion device 325 may expand to a pre-set shape, e.g., the pyloric occlusion device 325 may be formed of a self-expanding and/or shape memory material (see FIG. 4). As described below with respect to FIGS. 7, 7A, 8, 9A-9G and/or 10A-10B, when fully expanded (e.g., the sheath 305 is retracted in the proximal direction to fully release the pyloric occlusion device 325 in the patient), the pyloric occlusion device 325 may be configured for anchoring against the duodenum wall 335 and gastric wall 340, thereby blocking the pylorus (see FIG. 5). When the pyloric occlusion device 325 is fully deployed, the guidewire 320 may be retracted in the proximal direction, and the delivery device 300 may be removed from the patient.

In some embodiments, if the pyloric occlusion device 325 is to be removed, e.g., to allow stomach contents to flow through the pylorus, the medical professional may use another accessory, e.g., an end effector 250 and/or grasper tool, to remove the pyloric occlusion device 325. For example, in some embodiments, an argon plasma coagulation (APC) device may be used for detaching the pyloric occlusion device 325 from tissue ingrowth, and the pyloric occlusion device 325 may be removed by using a grasping tool. The pyloric occlusion device 325 may be configured for removal and retraction into the endoscope 240 (e.g., a working channel of the endoscope 240) by the end effector 250.

The pyloric occlusion device 325 may be configured in various embodiments in accordance with the present disclosure. Referring now to FIGS. 7, 7A, 8, 9A-9G and/or 10A-10B, exemplary embodiments of pyloric occlusion devices 700, 900, 905, 910, 915, 920, 925, 930 are shown. The pyloric occlusion device 325, 700, 900, 905, 910, 915, 920, 925, 930 may be formed of a self-expanding material, e.g., a shape memory material such as nitinol, and in some embodiments, may be braided. Although certain features may be described with respect to respective embodiments, it may be understood that a pyloric occlusion device in accordance with the present disclosure may be any combination of features described herein with respect to FIGS. 5-10B.

A pyloric occlusion device 700, e.g., a pyloric closure stent, may include a first flange 705 and a second flange 710 connected by a saddle 715, having a lumen extending along longitudinal axis 720. It may be understood that a flange may be any configuration so that a diameter of the flange is greater than a diameter of the saddle. For example, a flange may include any number of configurations, orientations, shapes, tapers, step ups, inflection points, etc. The pyloric occlusion device 700 may further include a closure element, as described below with respect to FIGS. 7, 7A, 8, 9A-9G and/or 10A-10B. The first and second flanges 705, 710 may be bulbs, expanding radially with respect to the longitudinal axis 720. The flanges and/or bulbs may be circular, spherical, semi-spherical, and/or elliptical, although other shapes are also envisioned. In some embodiments, the first flange 705 and/or the second flange 710 may include rounded portions 740, which may minimize tissue damage (e.g., perforation). In some embodiments, edges 706, 707 may extend from the first and/or second flanges 705, 710 in an outward direction (e.g., opposite from respective inner surfaces 745, 750) for manufacturing and/or for loading into the constrained position in a delivery device. The first flange 705 may have a first diameter d1 and a second flange 710 may have a second diameter d2. In some embodiments, the first and second diameters d1 and d2 may be equal, although in other embodiments (see FIGS. 9A-9B) the first and second diameters d1 and d2 may be different. It is understood that the first and second diameters d1 and d2 may be any size that exceeds the size of the opening of the pylorus, e.g., so the first and/or second flanges may contact the respective gastric wall and/or duodenum wall. The edges 706, 707 may form a diameter "d3," which may be less than first and/or second diameter d1, d2.

The saddle 715 may connect the first and second flanges 705, 710. In some embodiments, the saddle 715 may be hollow tube, which is then formed in a twisted shape to close the saddle 715. For example, a closure element may be configured to occlude a flow of material (e.g., stomach contents including food, liquid, and/or nutrients) through the saddle 715. The saddle 715 may be twisted, or rotated, about the longitudinal axis 720 as indicated by arrow 725 to create a kink, or closure element 730. In some embodiments, one of the first or second flanges 705, 710 may be rotated relative to the other of the first or second flange 705, 710, to create the closure element 730 in the saddle 715. In some embodiments, the first and second flanges 705, 710 may both rotate relative to each other in opposite directions to create the closure element 730 in the saddle 715. The rotation may be any amount to fully occlude the saddle 715, e.g., approximately 180° to approximately 720°. As described above, the pyloric occlusion device 700 may be formed of a braided nitinol material, which, when twisted, may result in a high density of braided material or wires (e.g., indicated at reference numeral 735) in the channel of the saddle 715 to form the occlusion. For example, the braided material may be concentrated at the closure element 730, and/or may have a higher density of material at the closure element 730.

The saddle 715 may be any length, indicated as "L4," e.g., to traverse the pyloric sphincter. In some embodiments, the saddle 715 may be approximately 5 mm to 25 mm, although it is envisioned that the saddle 715 may be any length, including less than 5 mm and/or greater than 25 mm to perform the desired procedure on a patient.

The nitinol braiding may be heat-set, so that the closure element 730 is pre-formed in the pyloric occlusion device 700. For example, as the pyloric occlusion device 700 is deployed, the saddle 715 may expand including the closure element 730, so that a portion of the pyloric occlusion device 700 is rotated as it is deployed and self-expands to the pre-set shape. It is also understood that in some embodiments, a pyloric occlusion device 700 may not be pre-set, so that the medical professional may partially deploy the pyloric occlusion device 700. For example, a portion of the pyloric occlusion device may be expanded (e.g., the first flange 705 and at least a portion of the saddle 715) while the remaining portion of the pyloric occlusion device remains in the sheath 305. The medical professional may then rotate the delivery device 300 to create a closure element 730 in the saddle 715. The remaining portion of the pyloric occlusion device 700 may then be delivered to expand the remaining portion of the saddle 715 and the second flange 710 (e.g., by retracting the sheath 305).

When deployed (see FIG. 5), an inner or proximal surface 745 of the first flange 705 may contact a surface of duodenum wall 335, for example, so that the first flange is deployed against the duodenum wall 335. Additionally, an inner or distal surface 750 of the second flange 710 may contact a surface of gastric wall 340, for example, so that the second flange is deployed against the gastric wall 340. The saddle 715 including the closure element 730 may extend between the duodenum wall 335 and the gastric wall 340 through the pylorus to block, or occlude, the pylorus.

Figure 6:
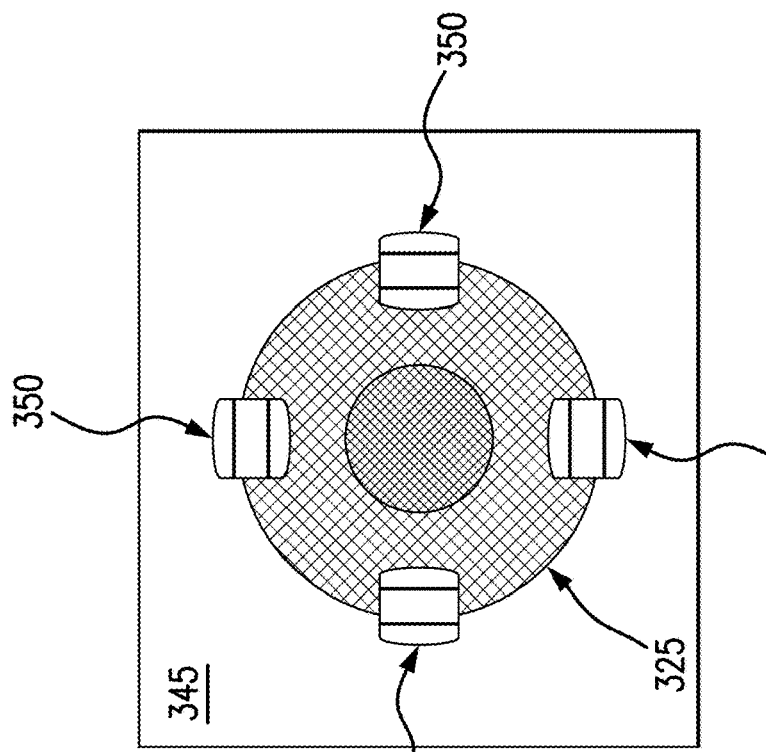
FIG. 6 illustrates an exemplary embodiment of a deployed pyloric occlusion device including an anchoring mechanism in accordance with the present disclosure.

The first and/or second flanges 705, 710 may anchor the device against the duodenum wall 335 and gastric wall 340 when the respective inner surfaces 745, 750 contact the walls 335, 340, so that pyloric occlusion device 700 is inhibited or prevented from migrating. In some embodiments, the first and/or second flanges 705, 710 may be attached to the walls 335, 340 by mechanical fasteners such as clips, sutures, and the like. As shown in FIG. 6, e.g., on a surface 345 of wall 340, one or more clips 350 (e.g., such as Boston Scientific's Resolution™ clip) may be deployed around the first and/or second flanges 705, 710. It is understood that the clips 350 may be deployable on the wall 335 in similar manner. The clips 350 may anchor the pyloric occlusion device 325, 700, 900, 905, 910, 915, 920, 925, 930, to further minimize and/or eliminate risk of migration of the pyloric occlusion device. In some embodiments, clips 350 may be deployed approximately 90° apart from each other around the first and/or second flanges 705, 710, although it is envisioned that any number of clips 350 may be utilized to anchor the first and/or second flanges 705, 710 to the walls 335, 340.

In some embodiments, pyloric occlusion device 700 may be fully coated, to minimize and/or prevent tissue ingrowth, and in other embodiments, a portion of the pyloric occlusion device 700 may be uncoated and other portions of the device 700 may be coated. An uncoated device 700 may be advantageous to later remove the pyloric occlusion device, e.g., with an argon plasma coagulation (APC) device, from the patient without having to disengage from duodenum and/or gastric tissue. In some embodiments, the saddle 715 may be uncoated to promote tissue ingrowth, which may be advantageous to anchor (e g, minimizing and/or preventing migration) the device 700 in tissue of the pylorus.

As shown in FIG. 7A, a coating may be applied to the first and/or second flanges 705, 710, while the saddle 715 remains uncoated. A coating 765 may be deposited on the first and/or second flanges 705, 710, and may extend from the respective edges 706, 707, to the respective rounded portion 740. In some embodiments, the coating may penetrate through the braiding of the device 700. A coating 765*a* on the first flange 705 may extend from the edge 706 to the rounded portion 740*a*. As mentioned, the first and/or second diameter d1, d2 for the first and/or second flange 705, 710 may be greater than the diameter d3 of the respective edge 706, 707. The coating 765*a*, 765*b* as applied may decreased in diameter to fill in and define an arcuate form. A second coating 765*b* may similarly be deposited on the second flange 710, extending from the edge 707 to the rounded portion 740*b*, filling in and defining an arcuate form. The coatings 765*a*, 765*b* may extend fully circumferentially around the respective flanges 705, 710. The coatings 765*a*, 765*b* may not affect the total length of the device 700, indicated as "L5." In some embodiments, the device may be approximately between 10 mm and 35 mm.

Figure 9B:
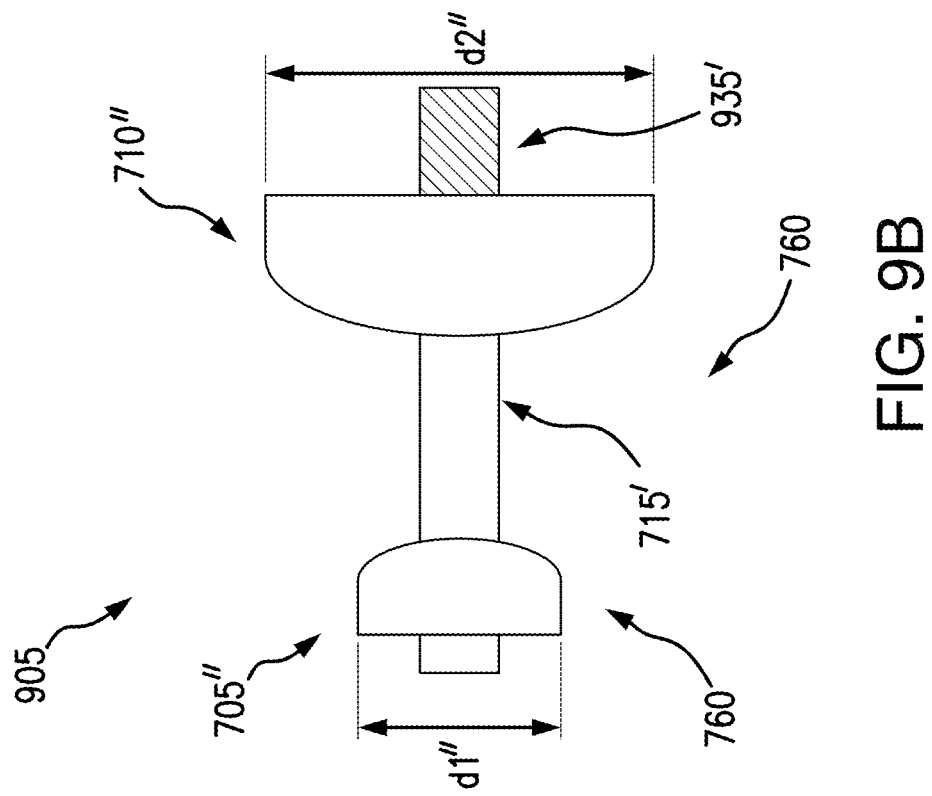
FIGS. 9A-9G illustrate exemplary embodiments of a pyloric occlusion device in accordance with the present disclosure.
Figure 9A:
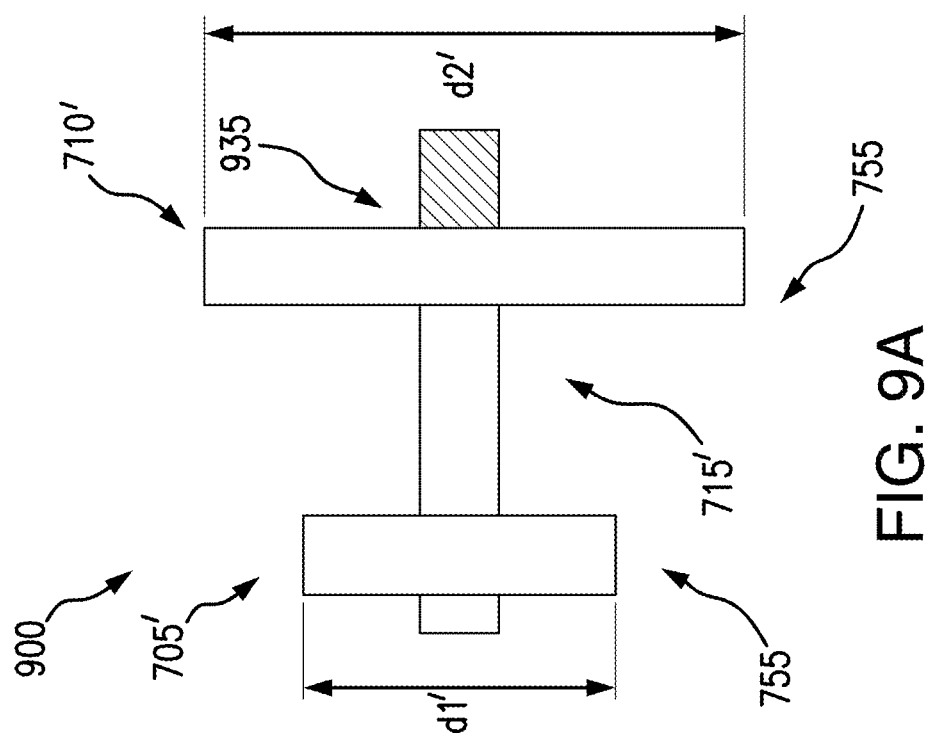

As described above, the first and/or second flanges 705, 710 may be sized and/or shaped according to various exemplary embodiments in accordance with the present disclosure, as shown in FIGS. 9A-9B, and/or 10A-10B. For example, a pyloric occlusion device may have a first flange 705', 705" having a first diameter d1', d1", and a second flange 710', 710" having a second diameter d2', d2", where the first and second diameters are different from each other. It may be advantageous to have a smaller flange 705', 705" in the duodenum, e.g., approximately 15-25 mm, and a larger flange 710', 710" in the gastric outlet, e.g., approximately 25-35 mm, as the duodenum may have less clearance than the gastric outlet. A larger flange at the gastric side may be needed to prevent migration against peristaltic forces, while a flange in the duodenum side may be sized to expand into the duodenum wall. In some embodiments, the first flange 705', 705" and/or the second flange 710', 710" may have square edges 755 and/or rounded edges 760. In some embodiments, as described below with respect to FIGS. 10A-10B, a first flange may be formed differently than a second flange.

FIGS. 9A-9B further illustrate another exemplary embodiment of a closure element in accordance with the present disclosure (e.g., an alternative to the closure element 730 of pyloric occlusion device 700). For example, pyloric occlusion devices 900, 905 may include a crimp, or swaged pin 935, 935', disposed on a proximal side of the pyloric occlusion device 900, 905 (e.g., the gastric wall 340 side). The saddle 715' may be a hollow tube, and the swaged pin 935, 935' may fully close the saddle 715' at the gastric wall 340 to occlude the pylorus when deployed. It may be advantageous to include a swaged pin 935, 935' to aide in removal as desired. For example, the medical professional may be able to better grasp the pyloric occlusion device 900, 905, via the swaged pin 935, 935'.

Figure 9D:
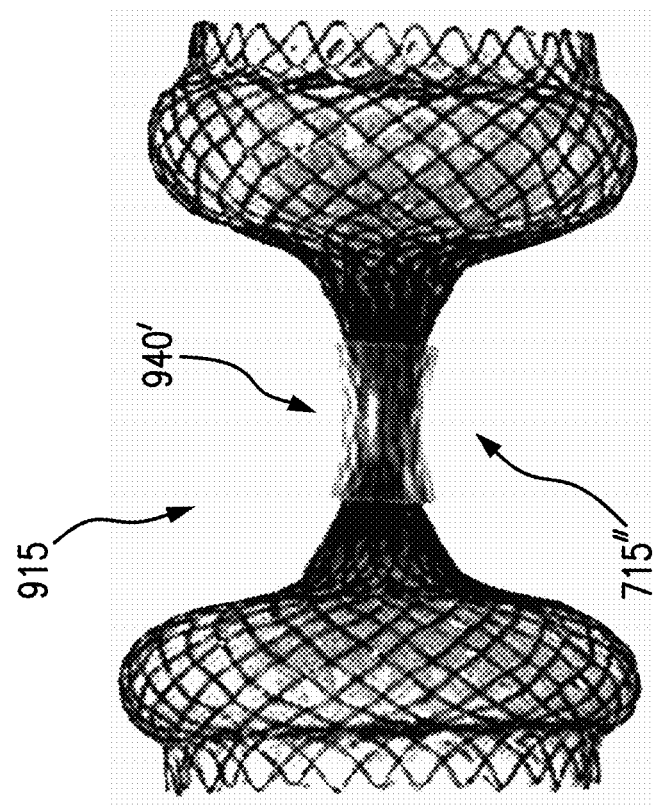
Figure 9C:
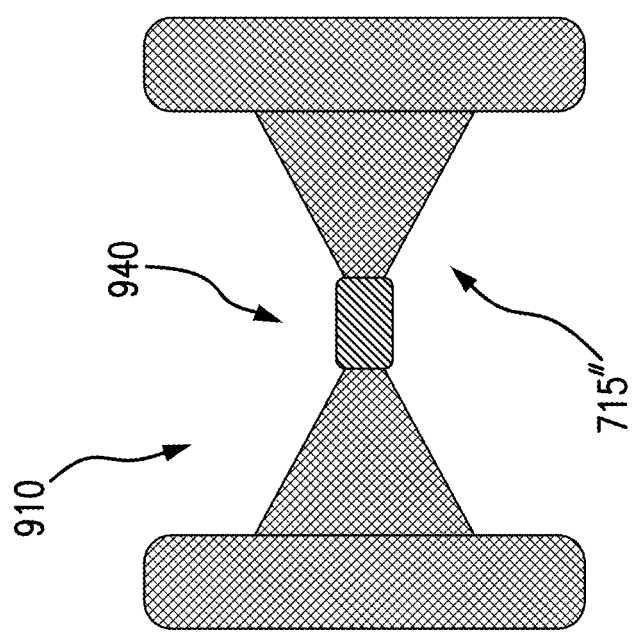

Referring now to FIGS. 9C-9D, a pyloric occlusion device 910, 915 may include a saddle 715" having a closure element as a fastener 940, 940' disposed at the saddle 715" to close the saddle 715" and occlude the pylorus. In some embodiments, the fastener 940 may be a suture, for example, wound around a portion of the saddle 715", to cinch and close the saddle 715". In some embodiments, the fastener 940' may be a heat shrink material, to create a closure in the saddle 715". In some embodiments, the fastener 950, 940' may be configured to hold the saddle 715" in a constrained shape. For example, the portion of the saddle 715" may be constricted by the fastener 940, 940' so that the saddle 715" may not expand. As such, the fastener 940, 940' may have a strength to withstand expansion forces of the saddle 715".

Figure 9F:
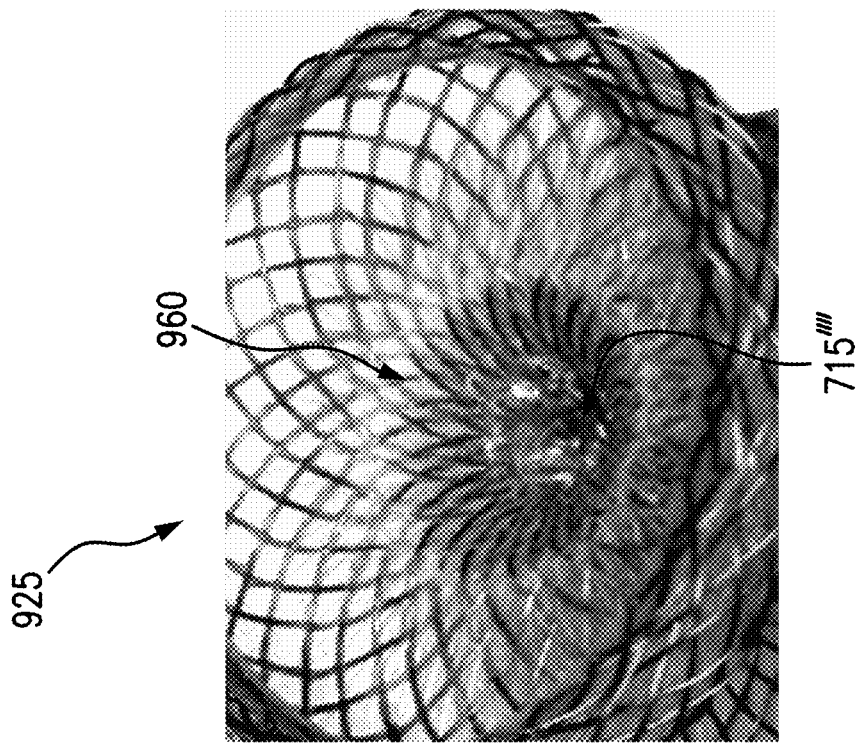
Figure 9E:
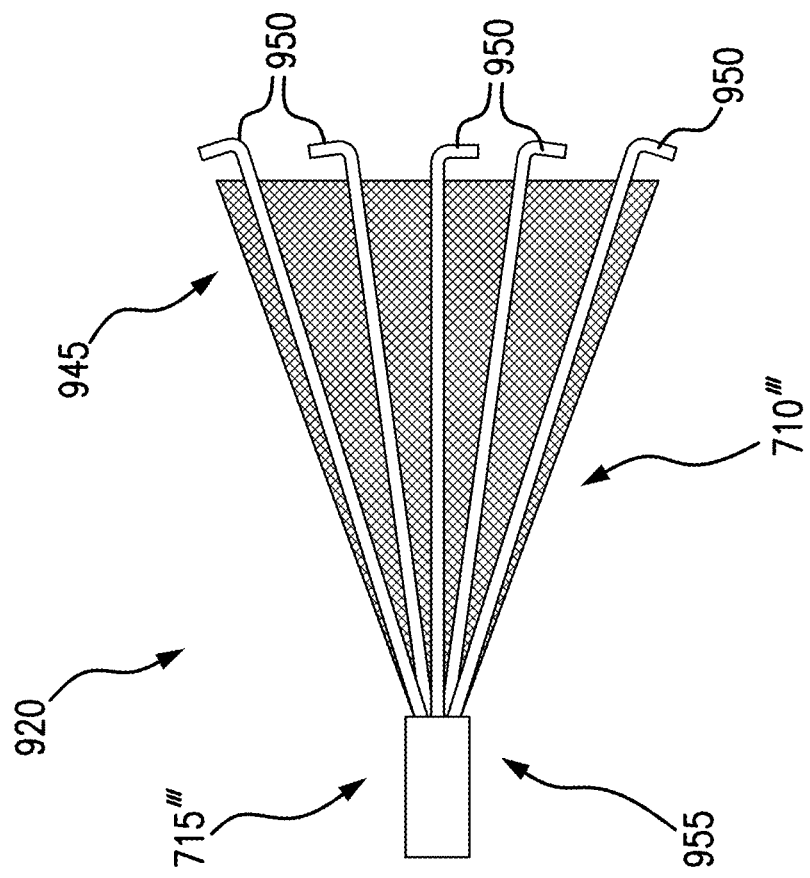

FIG. 9E illustrates an exemplary embodiment of a pyloric occlusion device 920 including a filter 945 as a closure element over a portion of the pyloric occlusion device 920. For example, Boston Scientific's Greenfield™ Vena Cava Filter, may be the filter 945 over a portion of the pyloric occlusion device 920. In some embodiments, the filter 945 may include a plurality of hooks 950 as fasteners extending longitudinally and circumferentially from a closure 955, so that the hooks 950 may engage with gastric wall 340 around a flange 710' and the closure 955 may be crimped around a portion of the saddle 715'''. The flange 710''' may be a frustoconical shape, with the filter 945 extending over the flange 715'''. The crimped portion of the saddle 715''' may be disposed at the duodenum wall 335 so that, for example, a portion of the frustoconical shape may anchor at the duodenum wall. In this instance, contact between the duodenum wall tissue and the pyloric occlusion device 920 may be a single circumferential ring.

FIG. 9F illustrates an exemplary embodiment of a pyloric occlusion device 925 including a plug 960 as a closure element disposed in a saddle 715'''' of the pyloric occlusion device 925. For example, the plug 960 may fill the saddle 715''''. In some embodiments, the plug 960 may be disposed in the saddle 715', to close the saddle 715' and occlude the pylorus. The plug 960 may be formed of silicone. In some embodiments, the plug 960 may be formed of a material to prevent tissue ingrowth around the nitinol braiding, and may be disposed in interstices of the braided nitinol of the first flange, second flange, or lumen, or combinations thereof. By making the plug 925 a portion of a coating extending continuously over the pyloric occlusion device, the plug 960 may be anchored to the pyloric occlusion device 925.

Figure 9G:
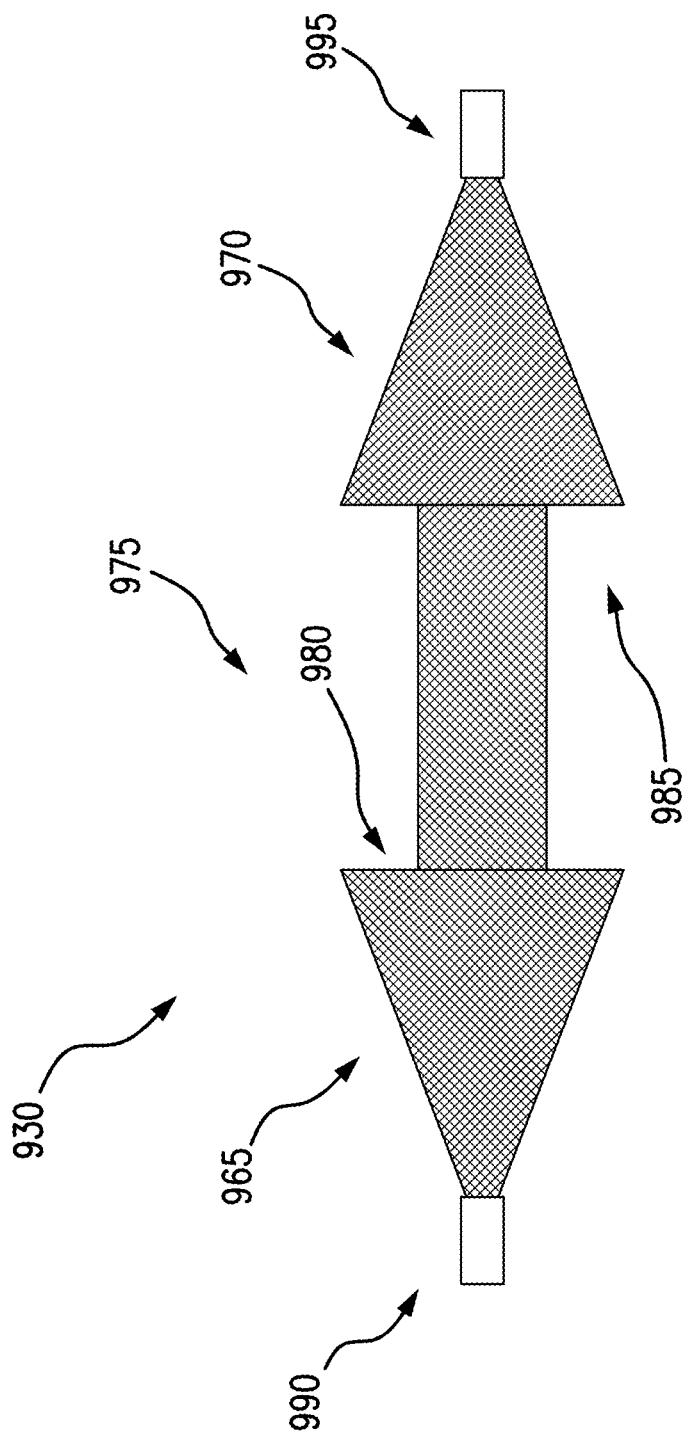

Referring now to FIG. 9G, a pyloric occlusion device 930 may include a first flange 965 and a second flange 970 connected by a lumen 975. The first and/or second flange 965, 970 may be formed in a frustoconical shape, so that the first flange 965 includes an inner surface 980 to contact the duodenum wall 335 and the second flange 970 includes an inner surface 985 to contact the gastric wall 340. The frustoconical shape of the first and/or second flange 965, 970 may anchor the device against the duodenum wall 335 and gastric wall 340 when the respective inner surfaces 980, 985 contact the walls 335, 340, so that pyloric occlusion device 930 is inhibited or prevented from migrating. The pyloric occlusion device 930 may include a first crimp 990, or swaged pin and a second crimp 995, or swaged pin as the closure element. The first crimp 990 may be disposed distal of the first flange 965, e.g., at a tip of the frustoconical flange 965. The second crimp 995 may be disposed proximal to the second flange 970, e.g., at a tip of the frustoconical flange 970. The first and/or second crimp 990, 995 may close the lumen 975 to occlude the pylorus. As described above, the first and/or second crimp 990, 995 may allow the medical professional, at a later time, to grasp the pyloric occlusion device 930 to ease removal.

Figure 7:
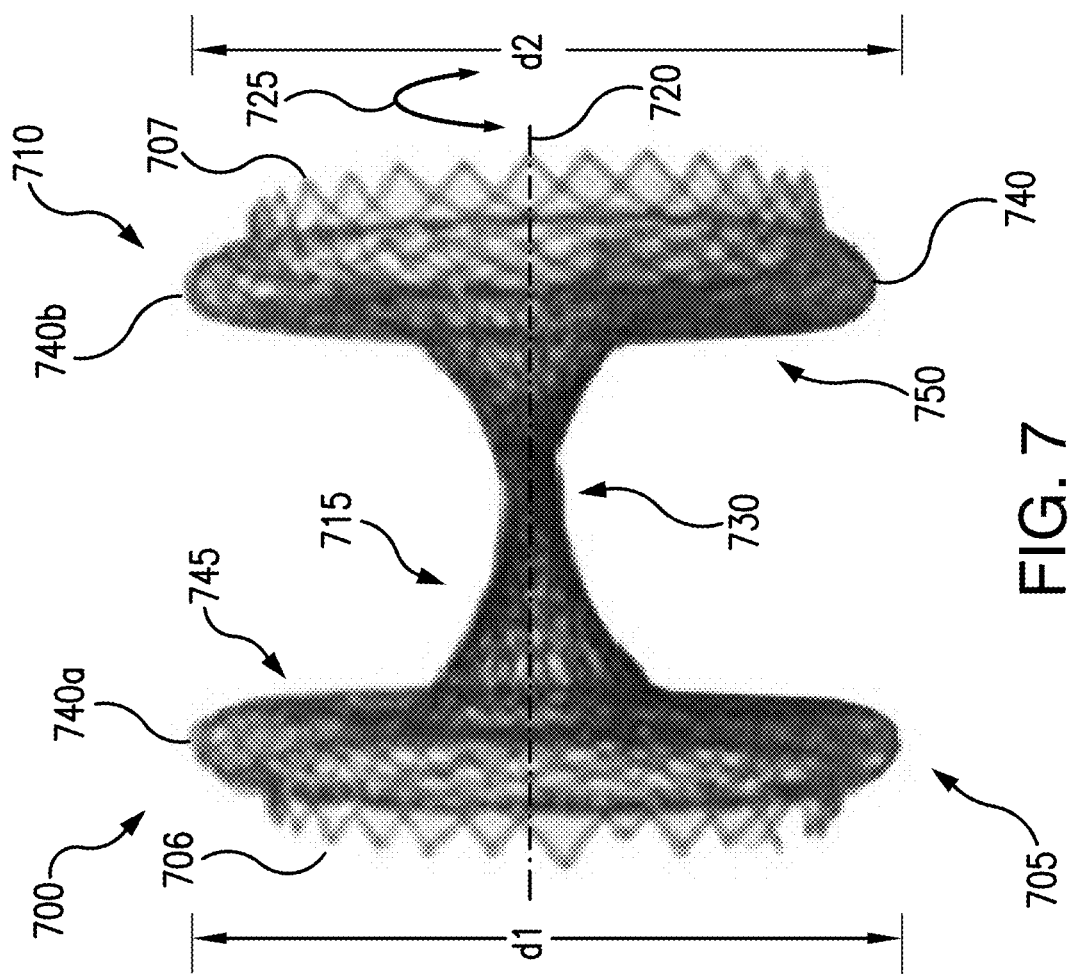
Figure 8:
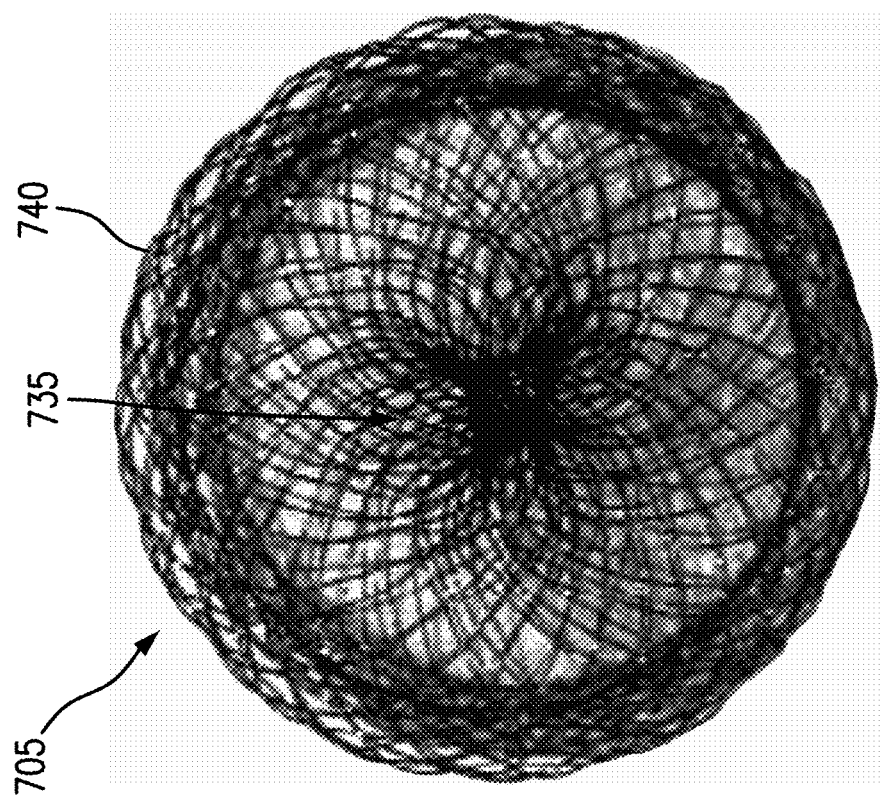
Figure 10A:
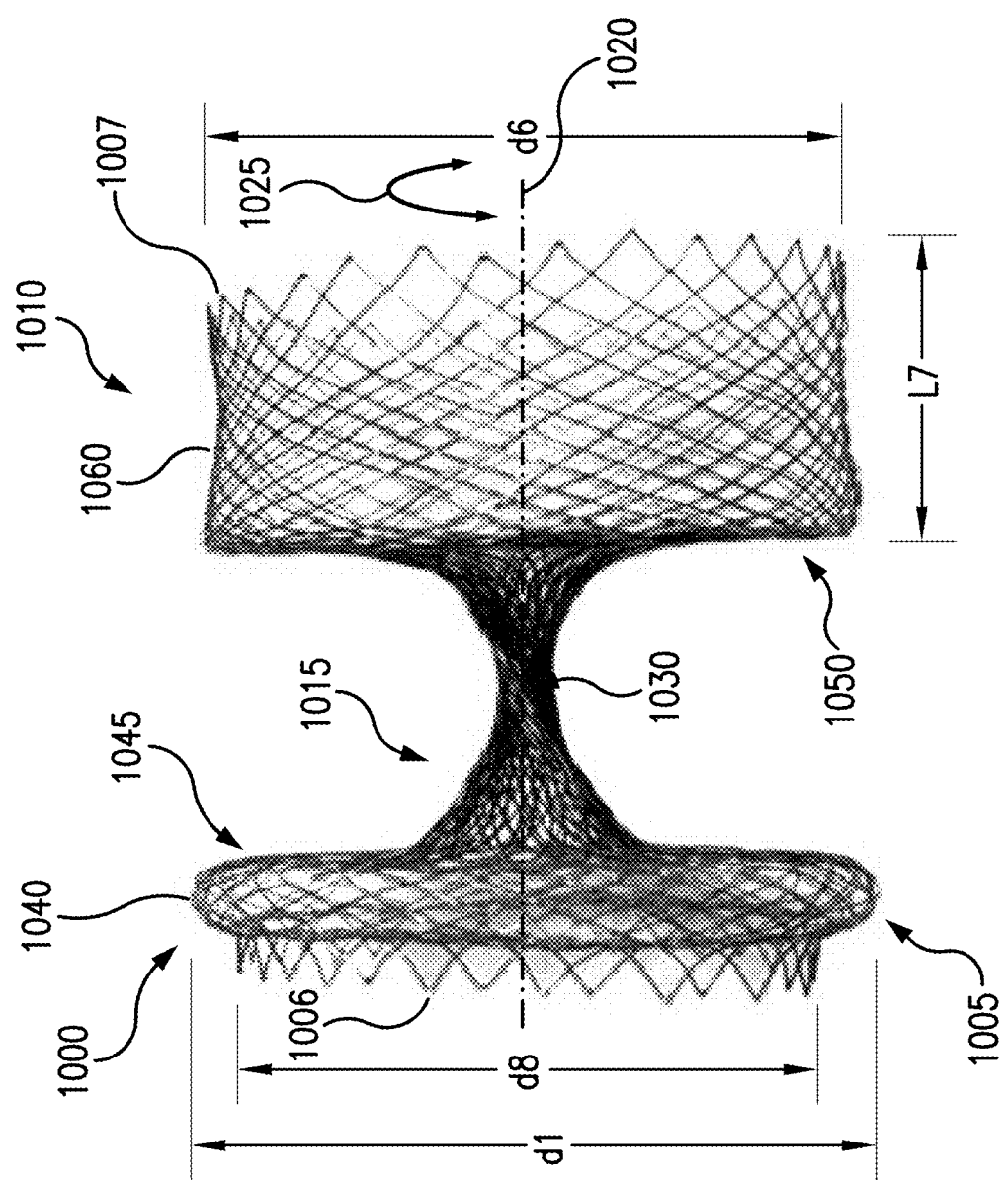
FIGS. 10A-10B illustrate an exemplary embodiment of a pyloric occlusion device in accordance with the present disclosure.
Figure 10B:
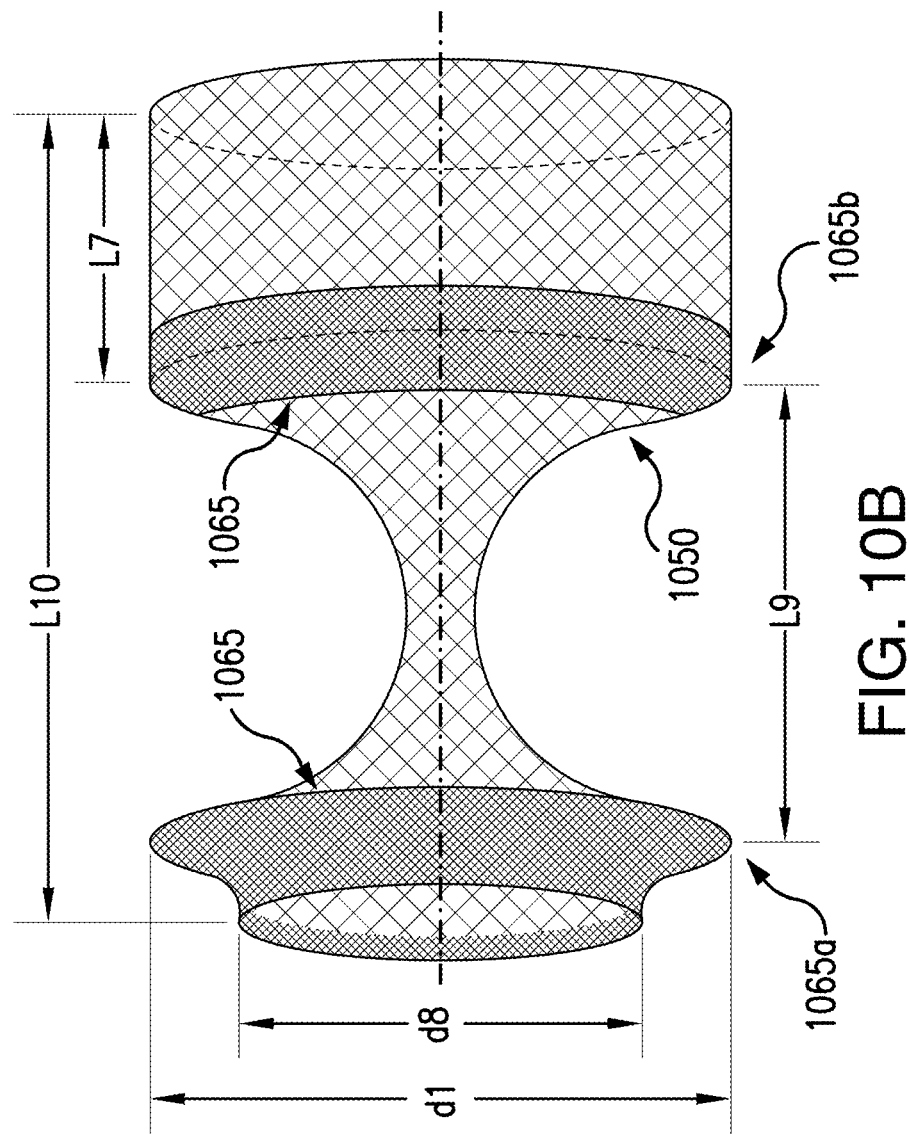

Referring now to FIGS. 10A-10B, another exemplary embodiment of a pyloric occlusion device 1000 in accordance with the present disclosure is shown. Pyloric occlusion device 1000, e.g., a pyloric closure stent, may include a first flange 1005 and a second flange 1010 connected by a saddle 1015, having a lumen extending along longitudinal axis 1020. It may be understood that a flange may be any configuration so that a diameter of the flange is greater than a diameter of the saddle. For example, a flange may include any number of configurations, orientations, shapes, tapers, step ups, inflection points, etc. The pyloric occlusion device 1000 may further include a closure element. The first flange 1005 may be a bulb, e.g., having a rounded portion 1040, expanding radially with respect to the longitudinal axis 1020. The second flange 1010 may be formed as a duodenal extension 1060. The bulb and/or extension may have a curvature to define a circumference. The bulb may be formed as circular, spherical, semi-spherical, and/or elliptical, although other shapes are also envisioned. In some embodiments, the first flange 1005 may include a rounded portion 1040, which may minimize tissue damage (e.g., perforation). In some embodiments, edge 1006 may extend from the first flange 1005 in an outward direction (e.g., opposite from inner surface 1045) for manufacturing and/or for loading into the constrained position in a delivery device. The first flange 1005 may be identical to the first flange 705 as shown in FIGS. 7-7A.

The duodenal extension 1060 as the second flange 1010 may be tubular, e.g., as an open stent, and having a length "L7," extending from inner surface 1050 in an outward direction along the axis 1020. The duodenal extension 1060 may extend the length L7 to an edge 1007. It may be advantageous to include a duodenal extension 1060 in a pyloric occlusion device to provide a holding force in the duodenum.

The first flange 1005 may have the first diameter d1 and the second flange 1010 may have a second diameter "d6." In some embodiments, the first and second diameters d1 and d6 may be equal, although in other embodiments (see FIGS. 9A-9B) the first and second diameters d1 and d6 may be different. It is understood that the first and second diameters d1 and d6 may be any size that exceeds the size of the opening of the pylorus, e.g., so the first and/or second flanges may contact the respective gastric wall and/or duodenum wall. The edge 1006 of the first flange 1005 may form a diameter "d8," which may be less than first diameter d1.

The saddle 1015 may connect the first and second flanges 1005, 1010. In some embodiments, the saddle 1015 may be hollow tube, which is then formed in a twisted shape to close the saddle 1015. For example, a closure element may be configured to occlude a flow of material (e.g., stomach contents including food, liquid, and/or nutrients) through the saddle 1015. The saddle 1015 may be twisted, or rotated, about the longitudinal axis 1020 as indicated by arrow 1025 to create a kink, or closure element 1030. In some embodiments, one of the first or second flanges 1005, 1010 may be rotated relative to the other of the first or second flange 1005, 1010, to create the closure element 1030 in the saddle 1015. In some embodiments, the first and second flanges 1005, 1010 may both rotate relative to each other in opposite directions to create the closure element 1030 in the saddle 1015. The rotation may be any amount to fully occlude the saddle 1015, e.g., approximately 180° to approximately 720°. As described above, the pyloric occlusion device 1000 may be formed of a braided nitinol material, which, when twisted, may result in a high density of braided material or wires (see e.g., FIG. 8 at reference numeral 735) in the channel of the saddle 1015 to form the occlusion. For example, the braided material may be concentrated at the closure element 1030, and/or may have a higher density of material at the closure element 1030.

The saddle 1015 may be any length, indicated as "L9," e.g., to traverse the pyloric sphincter. In some embodiments, the saddle 1015 may be approximately 5 mm to 25 mm, although it is envisioned that the saddle 1015 may be any length, including less than 5 mm and/or greater than 25 mm to perform the desired procedure on a patient.

The nitinol braiding may be heat-set, so that the closure element 1030 is pre-formed in the pyloric occlusion device 1000. For example, as the pyloric occlusion device 1000 is deployed, the saddle 1015 may expand including the closure element 1030, so that a portion of the pyloric occlusion device 1000 is rotated as it is deployed and self-expands to the pre-set shape. It is also understood that in some embodiments, a pyloric occlusion device 1000 may not be pre-set, so that the medical professional may partially deploy the pyloric occlusion device 1000. For example, a portion of the pyloric occlusion device may be expanded (e.g., the second flange 1010 and at least a portion of the saddle 1015) while the remaining portion of the pyloric occlusion device remains in the sheath 305. The medical professional may then rotate the delivery device 300 to create a closure element 1030 in the saddle 1015. The remaining portion of the pyloric occlusion device 1000 may then be delivered to expand the remaining portion of the saddle 1015 and the first flange 1005 (e.g., by retracting the sheath 305).

When deployed (see FIG. 5), an inner or proximal surface 1050 of the second flange 1010, e.g., as a duodenal extension 1060, may contact a surface of duodenum wall 335, for example, so that the second flange is deployed against the duodenum wall 335. Additionally, an inner or distal surface 1045 of the first flange 1005 may contact a surface of gastric wall 340, for example, so that the first flange is deployed against the gastric wall 340. The saddle 1015 including the closure element 1030 may extend between the duodenum wall 335 and the gastric wall 1040 through the pylorus to block, or occlude, the pylorus.

The first and/or second flanges 1005, 1010 may anchor the device against the duodenum wall 335 and gastric wall 340 when the respective inner surfaces 1045, 1050 contact the walls 335, 340, so that pyloric occlusion device 1000 is inhibited or prevented from migrating. In some embodiments, as described above, the first and/or second flanges 1005, 1010 may be attached to the walls 335, 340 by mechanical fasteners such as clips, sutures, and the like (see FIG. 6).

In some embodiments, pyloric occlusion device 1000 may be fully coated, to minimize and/or prevent tissue ingrowth, and in other embodiments, a portion of the pyloric occlusion device 1000 may be uncoated and other portions of the device 1000 may be coated. An uncoated device 1000 may be advantageous to later remove the pyloric occlusion device, e.g., with an argon plasma coagulation (APC) device, from the patient without having to disengage from duodenum and/or gastric tissue. In some embodiments, the saddle 1015 may be uncoated to promote tissue ingrowth, which may be advantageous to anchor (e g , minimizing and/or preventing migration) the device 1000 in tissue of the pylorus.

As shown in FIG. 10B, a coating may be applied to the first and/or second flanges 1005, 1010, while the saddle 1015 remains uncoated. A coating 1065 may be deposited on at least a portion of the first and/or second flanges 1005, 1010, and may penetrate through the braiding. On the bulb of the first flange 1005, the coating 1065 may extend from the respective edge 1006, to the respective rounded portion 1040. As mentioned, the first diameter d1 for the first flange 1005 may be greater than the diameter d8 of the edge 1006. The coating 1065a as applied may decrease in diameter to fill in and define an arcuate form. A second coating 1065b may be applied to a portion of the duodenal extension 1060. In some embodiments, the coating 1065b may be applied circumferentially around the duodenal extension 1060, and may be deposited at a transition from the inner surface 1050 to the duodenal extension 1060. In some embodiments, an edge 1007 of the duodenal extension 1060 may remain uncoated, although it is also envisioned that the coating may extend the length L7 of the duodenal extension. The coatings 1065a, 1065b may extend fully circumferentially around the respective flanges 1005, 1010. The coatings 1065a, 1065b may not affect the total length of the device 1000 may, indicated as "L10." In some embodiments, the device 1000 may be approximately between 10 mm and 50 mm.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the subject matter of the claims.

What is claimed is:

1. A pyloric occlusion device for deployment in an endoscopic procedure, comprising:
   a first flange configured to anchor the device with respect to a duodenum wall;
   a second flange configured to anchor the device with respect to a gastric wall and connected to the first flange by a saddle region having a lumen, the second flange being proximal to the first flange; and
   a closure, wherein the closure is configured to fully occlude a flow of material through the lumen upon deployment of the device.

2. The pyloric occlusion device according to claim 1, wherein the closure is a closure of the lumen by rotation of one of the first or second flange relative to the other of the first or second flange, or by rotation of the first and second flange opposite of each other.

3. The pyloric occlusion device according to claim 1, wherein the closure is any of the following:
   a swaged pin disposed proximal to the second flange;
   a fastener;
   a plug to fill the lumen; or
   a filter, the filter including one or more hooks extending from the saddle region.

4. The pyloric occlusion device according to claim 1, wherein the first flange includes a bulb and the second flange includes a duodenal extension.

5. The pyloric occlusion device according to claim 1, wherein a first diameter of the first flange is equal to a second diameter of the second flange.

6. The pyloric occlusion device according to claim 1, wherein a first diameter of the first flange is different from a second diameter of the second flange.

7. The pyloric occlusion device according to claim 1, further comprising one or more mechanical fasteners disposed around the second flange for anchoring the second flange to tissue.

8. The pyloric occlusion device according to claim 1, wherein a covering is disposed on a least a portion of the first flange, second flange, or lumen, or combinations thereof, for preventing tissue ingrowth.

9. The pyloric occlusion device according to claim 8, wherein the covering comprises a membrane, sleeve, or coating, or combinations thereof.

10. The pyloric occlusion device according to claim 1, wherein the pyloric occlusion is deployable across a pylorus with the saddle region bridging the pylorus, the first flange anchored against a duodenum side of the pylorus, the second flange anchored against a gastric side of the pylorus, and the closure operable to fully occlude the flow of material through the pylorus.

11. The pyloric occlusion device according to claim 10, wherein the pyloric occlusion device is removable to allow flow of material through a pylorus.

12. A system for delivering an occlusion device to a pylorus in an endoscopic procedure, the system comprising:
   a delivery device including an inner member having a guidewire and a retractable outer sheath, the inner member and the outer sheath being operable to constrain the occlusion device therebetween prior to deployment;
   wherein the occlusion device includes:

a first flange;

a second flange connected to the first flange by a saddle region having a lumen, the second flange being proximal to the first flange; and a closure, wherein the closure is configured to fully occlude a flow of material through the lumen upon deployment of the device across the pylorus.

13. The system according to claim 12, wherein the closure is a closure of the lumen by rotation of one of the first or second flange relative to the other of the first or second flange, or by rotation of the first and second flange opposite each other.

14. The system according to claim 12, wherein the closure is any of the following:
   a swaged pin disposed proximal to the second flange;
   a fastener;
   a plug to fill the lumen; or
   a filter, the filter including one or more hooks extending from the saddle region.

15. The system according to claim 12, wherein the pyloric occlusion is deployable across a pylorus with the saddle region bridging the pylorus, one of the first flange or the second flange being anchored against a duodenum side of the pylorus, the other of the first flange or the second flange anchored against a gastric side of the pylorus, and the closure operable to fully occlude the flow of material through the pylorus.

16. A method for delivering an occlusion device to a pylorus in an endoscopic procedure, the method comprising:
   inserting an endoscope in a stomach of patient;
   deploying a delivery device through the endoscope to a position proximal to the pylorus for delivering the occlusion device across the pylorus, the delivery device including a sheath for holding the occlusion device in a constrained configuration;
   extending the delivery device at least partially through gastric tissue through the pylorus; and
   retracting the sheath to deploy a first flange on a duodenal side of the pylorus, and retracting the sheath further to deploy a second flange on a gastric side of the pylorus, wherein the first flange and the second flange are connected by a saddle region having a lumen;
   wherein the occlusion device includes a closure operable to fully occlude a flow of material through the pylorus upon deployment of the device across the pylorus.

17. The method according to claim 16, further comprising removing the occlusion device from the pylorus.

18. The method according to claim 16, wherein the closure is any of the following:
   a closure of the lumen by rotation of one of the first or second flanges relative to the other of the first or second flange;
   a swaged pin disposed proximal to the second flange;
   a fastener;
   a plug disposed in the lumen; or
   a filter, the filter including one or more hooks extending from saddle region.

19. The method according to claim 16, wherein the first flange includes a bulb and the second flange includes a duodenal extension.

20. The method according to claim 16, further comprising one or more mechanical fasteners disposed around the second flange for anchoring the second flange in tissue.

* * * * *